United States Patent [19]
Prosl

[11] Patent Number: 5,954,691
[45] Date of Patent: Sep. 21, 1999

[54] HEMODIALYSIS ACCESS APPARATUS

[75] Inventor: Frank R. Prosl, Duxbury, Mass.

[73] Assignee: Biolink Corporation, Middleboro, Mass.

[21] Appl. No.: 08/485,498

[22] Filed: Jun. 7, 1995

[51] Int. Cl.$^6$ ................................................. A61M 11/00
[52] U.S. Cl. ........................................... 604/93; 604/169
[58] Field of Search ................................. 604/9, 93, 167, 604/169, 175, 247, 256

[56] References Cited

U.S. PATENT DOCUMENTS

| | | |
|---|---|---|
| 4,243,034 | 1/1981 | Brandt ..................................... 604/169 |
| 4,994,042 | 2/1991 | Vadher .................................... 604/165 |
| 5,041,098 | 8/1991 | Loiterman et al. . |
| 5,053,013 | 10/1991 | Ensminger et al. ..................... 604/167 |
| 5,057,084 | 10/1991 | Ensminger et al. . |
| 5,090,954 | 2/1992 | Geary . |
| 5,176,653 | 1/1993 | Metais . |
| 5,180,365 | 1/1993 | Ensminger et al. . |
| 5,226,879 | 7/1993 | Ensminger et al. . |
| 5,263,930 | 11/1993 | Ensminger . |
| 5,281,199 | 1/1994 | Ensminger et al. . |
| 5,350,360 | 9/1994 | Ensminger et al. . |
| 5,356,381 | 10/1994 | Ensminger et al. . |
| 5,417,656 | 5/1995 | Ensminger et al. . |
| 5,421,814 | 6/1995 | Geary . |
| 5,476,451 | 12/1995 | Ensminger . |
| 5,520,643 | 5/1996 | Ensminger et al. . |
| 5,527,277 | 6/1996 | Ensminger et al. . |
| 5,527,278 | 6/1996 | Ensminger et al. . |
| 5,556,381 | 9/1996 | Ensminger et al. . |
| 5,562,617 | 10/1996 | Finch et al. . |

FOREIGN PATENT DOCUMENTS

WO/96/25196  8/1996  WIPO .

OTHER PUBLICATIONS

H. My et al., Letter, 21 (13) La Presse Medicale (Apr. 4, 1992) 630 (with translation) and—H. My et al., Use of the Implantation Site Technique in Chronic Hemodialysis, 15 Nephrologie (1994) 173–174 (with translation).

D.W. Windus Permanent Vascular Access: A Nephrologists View, 21(5) Am. J. Kidney Diseases (May 1993) 457–71.

A.J. Bleyer et al., The Costs of Hospitalizations Due to Hemodialysis Access Management, 9(1) Nephrology News & Issues 19–22 (Jan. 1995). Part of a symposium issue. All the other articles of the same issue are also enclosed.

G.A. Beathard, Treatment of Vascular Access Graft Dysfunction, 1(2) Adv. Renal Realignment Therapy (Jul. 1994) 131–147.

H.I. Feldman et al., Hemodialysis Vascular Morbidity, 7 J. Am. Soc'y Nephrology (1996) 523–35.

(List continued on next page.)

*Primary Examiner*—Michael A. Brown
*Attorney, Agent, or Firm*—Jerry Cohen

[57] ABSTRACT

An implanted single- or dual-lumen device for repeated accessing of a vessel within a body, especially for hemodialysis, plasmapheresis, and other fluid exchange therapy treatments. The device is characterized by having: no septum for sealing but uses a resilient material to form a seal; a smooth streamlined flowpath; low flow resistance; substantially no stagnation points, such that the device is easily and completely flushed; and a positive locking mechanism that accepts and retains a matching needle apparatus. The device is joined to a catheter, in most cases, such that fluids can be extracted from or injected into the vessel to be accessed. The device is designed for the high flowrates, on the order of 400 milliliters per minute, associated with hemodialysis, plasmapheresis, and other fluid exchange therapies. A corresponding straight-needle apparatus is designed to mate and lock with the access device, where alignment and open flowpath is ensured. The needle apparatus first penetrates the skin and then the access device via the seal. The access device is flexibly mounted to the body at the attached catheter allowing the access device itself to move under the skin so as to accommodate and align with the needle apparatus.

25 Claims, 8 Drawing Sheets

OTHER PUBLICATIONS

T.L. Swan et al. Pulmonory Embolism Following Hemodialysis Access Thrombosis, 91 J. Vascular & Interventional Radiology (Sep.–Oct., 1995) 683–86.

D.W. Butterly et al., Hemodialysis Vascular Access: Effect on Kinetics and the Dialysis Prescription, 16 Am. J. Nephrology (1996) 45–51.

M.V. Rocco, et al., 28 (2) Am. J. Kidney Disease (Aug. 1996) 250–56.

G. Dunea, et al, 37 Asaio Trans'ns (1991) 276–77.

G.S. Beachard 6(6) J. Am. Soc'y Nephrology (1995) 1619–24.

C. Lefton, Maintaining Dialysis Fistulas and Grafts: A Review, Nephrology News & Issues (Jan. 1997) 10–12;O and.

D.W. Windus et al., Prosthetic Fistula Survival and Complications in Hemodialysis, 20 Am.J. Kidney Diseases 448–52.

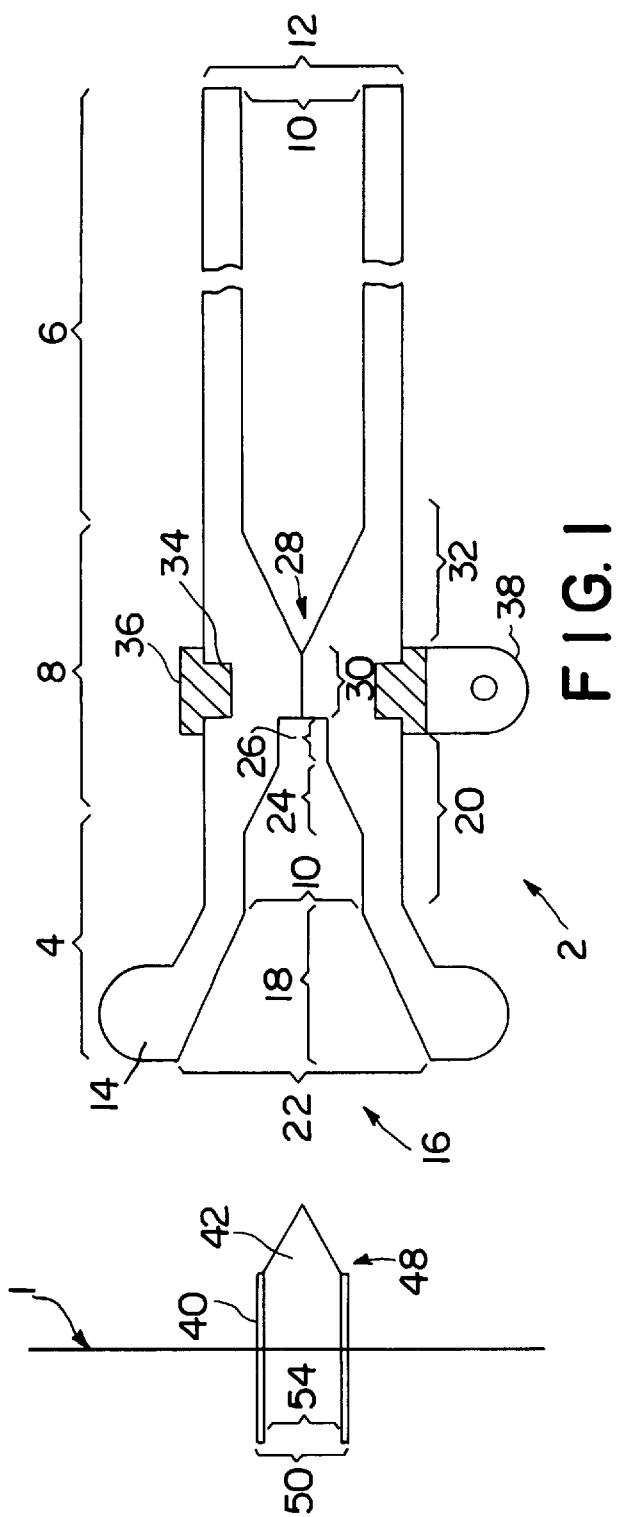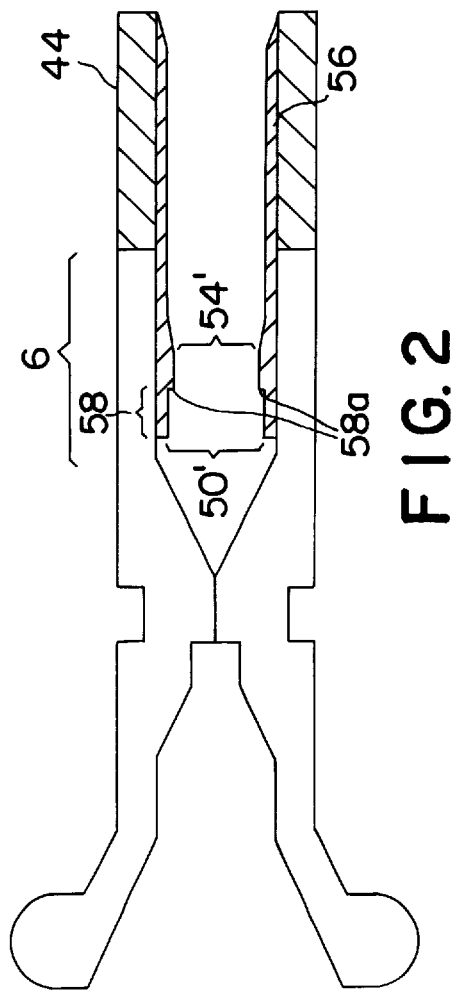

HEMODIALYSIS ACCESS APPARATUS

FIELD OF THE INVENTION

The present invention relates generally to apparatus that allows access to the vascular system of a human (or other animal) for the high-volume fluid flow required in hemodialysis, plasma-pheresis, and other fluid exchange therapies. More particularly, the present invention relates to a septum-less subcutaneously implanted access of single- or dual-lumen construct and a mating needle apparatus.

BACKGROUND OF THE INVENTION

There exists a class of devices for accessing fluid spaces and vessels within a human (or animal) body that are generally referred to as "ports". Herein, "vessel" is defined as any conduit carrying a fluid within the patient's body. These prior art devices comprise a chamber having an access opening sealed by means of a septum and having an egress from a second location leading to a catheter disposed within a fluid space or vessel. The septum allows a needle to pass into the chamber, but then closes when the needle is removed, thereby preventing fluid leakage from within a space or vessel and also anything from entering or exiting the chamber. These devices are usually implanted below the skin to prevent infection, other contamination, and mishandling.

Ports are designed for relatively infrequent use, perhaps once a week, and, importantly, for flowrates of 50 milliliters per minute or less, as is common during chemotherapeutic treatment. Modification of these devices for hemodialysis, plasma-pheresis, and other fluid exchange therapies, which require much greater flowrates, by simply enlarging the device components, poses several serious drawbacks that effectively limit use in such applications. First, the septum degrades quickly due to the larger gauge needles necessary to accommodate the flowrates required in hemodialysis. Repeated puncturing of the septum by these large needles produces numerous free-floating septum fragments that can find their way into the circulatory system. Accordingly, the useful life of the devices is substantially shortened, thereby defeating one of the purposes of using an implanted subcutaneous device. Second, the flowpath has several stagnation points where clots may form and also is not completely flushable or easily cleaned, thereby providing breeding grounds for infection, once contaminated or a build-up of material which may adversely affect function. Third, the flowpath is not streamlined and contains flowpath obstructions, sharp corners, and abrupt changes in flow area and flow direction. This tends to increase the shear stress and turbulences experienced by blood flowing through the device due to the significantly higher flowrates required in hemodialysis, thereby increasing erythrocyte damage and platelet activation. Also, the tortuous flowpath increases the pressure drop through the devices, which can increase air release and foaming, causing the dialysis machine's safety alarms to activate.

Typical access port apparati are disclosed in U.S. Pat. Nos. 5,180,365 (Jan. 19, 1993), 5,226,879 (Jul. 13, 1993), 5,263,930 (Nov. 23, 1993), and 5,281,199 (the '199 patent) (Jan. 25 1994); all entitled "IMPLANTABLE ACCESS DEVICES" and all issued to William D. Ensminger as either the sole or the first-named inventor. Only the '199 patent is assigned, that assignment being to Michigan TransTech Corporation of Ann Arbor, Mich. The following discussion concerns the (assigned) '199 patent; while all of the references are relevant, the '199 patent embodies the most recent material and also incorporates material from each of the earlier patents.

The devices described in the '199 patent include a funnel-shaped entrance to an access housing, which is fixed to the surrounding tissue. The housing is connected to an articulated valve, which is in turn joined to a catheter. Several types of valves are disclosed, including one that is a tube fabricated in a flattened shape that is forced open by the insertion of a filament. Other valves disclosed include manually activated types. In these manual valves, manual actuation applied to the skin and translated to the device moves two disks which slide over and in contact with each other to align holes in those disks. A needle may be inserted when the holes are aligned; the disks secure the needle in the housing when the external manual pressure is released. This patent also discloses a curved entry (presumably to allow the needle to enter at a convenient angle to the skin but still align parallel to the vessel). The disclosure of this patent, in column 9, line 53, mentions use in hemodialysis treatment.

The Ensminger et al. '199 device has several characteristics which lead to problems. First, in most embodiments the curved needle must be flexible, and as such can kink or otherwise restrict flow. However, when the needle is inserted, no such kink can be seen by the operator, and may not be detected before damage to the patient results. Another drawback of these devices can best be seen by inspection of FIG. 1A of the '199 patent, showing an abrupt change in flow diameter where the catheter 46 is joined to the valve 24. Abrupt changes form space for fluid stagnation to occur and/or eddy currents that promote clot formation. Further, such spaces are not easily flushed due to the lack of a streamlined flowpath. This same problem is shown in FIG. 1A of this patent in the stagnant space around the leaf valves 38. Indeed, such problems exist at nearly every transition point between the various structures and assemblies of the '199 device.

A further drawback of the '199 device is the attachment of the housing to the surrounding tissue. Since the housing cannot move to accept a rigid needle, the needle must be closely aligned with the port entrance. Otherwise, the needle must be moved transversely under the skin causing discomfort for the patient. Ensminger et al. required the use of a flexible tube to solve this problem. A still further drawback of the '199 apparatus is shown in FIGS. 41–43. These drawings show needle points where the flow has a radial direction component as it leaves the needle. This change of direction, especially under high flowrates, can severely damage hematocytes and activate platelets. Also, the flexible tube will have a greater flow resistance and higher shear than a rigid straight needle having a similar outside diameter.

A general limitation in all relevant prior art devices is the lack of a streamlined flowpath. Without such streamlining, stagnant volumes exist where clots may form and shear stress is higher, tending towards erythrocytic damage. Such locations cannot be flushed or easily cleaned. Blood residue remaining in the devices after flushing may clot and provide breeding grounds for infection, once contaminated. In addition, pressure drops and abrupt flow direction changes may damage blood components.

The Ensminger '199 device is still further limited by its lack of effective sealing provisions. There is no force urging the valve to seal. The valve is therefore not fault-tolerant and particles, clots, skin fragments, and imperfections on the inside surface of the valve will cause leakage. In addition, the valve opens in response to very low changes in pressure. Further, the seal is in line with the housing, making the device longer and increasing the changes in pressure experienced by fluids passing through the device. Finally, there is no locking mechanism whereby the needle may be secured to the device.

Accordingly, it is an object of this invention to overcome the above illustrated inadequacies and problems of extant devices by providing a totally implantable access means suitable for repeated use in applications (e.g., hemodialysis with blood flowrates of 250 milliliters per minute or more yet with low pressure drops along the flowpath.

It is another object of this invention to provide a laminar flowstream, even during flow diameter transitions.

It is a further object to provide means where the flowpath is streamlined and provides substantially no stagnation points, and also to provide an apparatus where the entire flowstream is flushable.

It is a still further object of this invention to provide apparatus suitable for single- and dual-lumen catheter systems.

It is yet another object of this invention to provide an access housing that is less painful during needle insertion and more accommodating during dialysis for the patient.

It is a further object to secure the needle within the access housing during the dialysis session.

It is another object of the invention, when using dual-lumen catheters to secure both needles to each other.

It is a still further object to have lower clotting, stenosis, and infection rates than synthetic grafts.

It is yet another object to have lower infection and lumen clotting than percutaneous catheters.

SUMMARY OF THE INVENTION

The foregoing objects are met by a subcutaneously implantable device for accessing a vessel within a patient's body, the device including (a) an access guidance means having a through channel and (b) a catheter having a through channel and comprising an access portion, a sealing portion, and a distal portion. A resilient means for sealing is arranged within the sealing portion of the catheter. The resilient means for sealing ordinarily prohibits fluids from passing the seal. But when a mechanical device is inserted percutaneously, and guided to the catheter's access portion by the access guidance means, the mechanical device passes through the access portion of the catheter, engages the sealing means, and pushes it open. This provides access to the catheter's distal portion and, ultimately, the vessel lumen, as the distal portion of the catheter, distal from the access guidance means, extends into a vessel lumen. The catheter is attached to the surrounding tissue supporting the catheter, but the access guidance means's position is not fixed relative to the tissue.

The means for sealing includes, in a preferred embodiment, a tube made of a resilient material, which incorporates a valving feature within the tube lumen. The tube is disposed axially along the inner wall of the channel. A spring clamp is provided adjacent to and external of the tube and acts to compress the tube such that the tube's inner lumen is closed, thereby preventing fluids from passing.

The spring clamp is arranged and constructed to close the tube's lumen such that the longitudinal transition profile from the open to the closed position forms a particular shape. The shape of the valve allows for the conical point of the needle obdurator to open or push apart the rubber valve slit in a wedging action as the needle is pushed through the seal. The needle pushing force overcomes the spring biasing force and the seal's internal stresses as the needle enters the sealing area without cutting the rubber. Because no cutting occurs, no rubber particles are generated, as seen with septa in ports. Furthermore, the number of penetration cycles to failure is very high, as negligible damage occurs during penetration.

The flowpath transitions between the needle, the tube lumen, and a catheter are arranged and constructed to provide for maximum smoothness and continuous flowpaths without abrupt changes in flow diameter and only gentle changes in flow direction. All narrowing and broadening of the flowpath is gradual, with angles of 25 degrees or less.

The invention also provides for a hollow needle apparatus that matingly corresponds to the through channel of the access device, and an obdurator that is inserted into the lumen of the needle, filling the lumen. This needle/obdurator combination provides a needle assembly with a pointed end, and an outer surface having smooth transitions, which are formed to puncture tissue easily and to open the valve without damaging it.

The needle apparatus further includes a circumferential groove formed into a sector of the needle's outer surface of approximately 180°. A spring lock is positioned within the access housing channel upstream from the resilient sealing means, engaging the groove to secure the needle to the access device when the needle is in the correct axial position. The groove and spring lock are designed to disengage when the needle is rotated approximately 90°, allowing the needle to be extracted from the housing.

Another preferred sealing means includes a fixed axial seating mount affixed to the through hole inner wall distally from said sealing location, the seating mount having passages to allow fluid to pass. A movable valve poppet is upstream from and fixed to said seating mount to prevent radial movement yet allow axial movement of the needle. A compression spring in said seating mount acting on said movable valve poppet provides a force pushing said valve poppet longitudinally against a valve seat. The movable valve poppet is designed with a surface that mates with a surface on the tube's inner wall (i.e., valve seat). A seal is provided between the mating surfaces of the tube inner wall and the movable valve poppet, such that the spring biasing force pushes the two mating surfaces together and the seal therebetween prevents flow from passing. The movable valve poppet has a proximally facing surface designed to engage the needle. Pushing the needle into the device's flowpath against the poppet, which overcomes the spring force, moving the poppet away from the sealing surface, thereby opening the valve sealing means and allowing fluid to pass through the access. The needle may be secured in the device by the groove and locking means arrangement, as described earlier.

Another sealing means includes a resilient balloon adjacent to the through channel. The balloon has a septum suitable for penetration by a fine needle. A fluid is introduced through the fine needle to inflate the balloon. The inflated balloon traverses the through channel, contacting the opposing side of the through channel, and thereby closing said hole and preventing any liquids from passing. Alternatively, the balloon may be arranged around the circumference of the through channel, and closes the through channel when inflated.

The presently claimed access device is suitable for both single-needle and standard hemodialysis, plasmapheresis, and fluid exchange therapy applications. For standard applications, which require two flowpaths, the housing may be arranged and constructed to engage two needle assemblies, as described above, and include dual-lumen through channels. When two needles are used, a spring-loaded bar may be provided that engages each needle, thereby locking both needles to each other to preclude inadvertent disconnection of only one needle, thereby enhancing patient safety.

It is important to note that the primary object of this invention is to provide an implantable, subcutaneous access device suitable for applications requiring flow rates of 250 ml/min or greater, with low pressure drops along a streamlined flowpath having substantially no stagnation points. Low pressure drops and substantial elimination of stagnation points are achieved by having smooth transition points where different elements of the device abut (e.g., the channel-catheter interface) and by having all changes in lumen diameter be of a gradual nature and having straight or nearly straight flowpath without sharp curves or objects protruding into the flowpath and no dead volume.

Because such large flowrates are desired with low resistance, it is necessary to have the largest needle outside diameter that patients will accept. Accordingly, rigidity of the puncture needle is desired. A rigid needle allows a greater inner lumen diameter per outer component diameter (i.e., thinner walls) than does a flexible tube. This is important because it allows the needle to be as small as possible, thereby lessening the trauma on the patient's puncture site, yet still be capable of handling large flowrates. Flexible tubes have a much higher outer diameter to inner diameter aspect ratios. Thus, to accommodate the bloodflows common during hemodialysis, a much larger outer diameter would be required if flexible materials were used. Also, a rigid needle allows a greater force to be transmitted to the seal to overcome the resistant force generated by the spring. Thus, a greater resistant force can be employed, resulting in a more robust, reliable, and fault-tolerant seal.

Further, the lack of sharp angles or bends in the flowpath is much less injurious to fragile hematocytes. Since the flowpath from needle to catheter (or vice versa) is substantially straight, the turbulence is minimized, and the shear stresses lessened, resulting in less erythrocyte damage and a lowered tendency toward platelet activation.

Finally, it is anticipated that a medically acceptable, water-based lubricant will be used on the needle exterior, as a diminished device lifespan of 100–150 cycles has been observed when no lubricant is used. Lifespan should be very long when properly lubricated needles are used for each insertion.

Other objects, features and advantages will be apparent from the following detailed description of preferred embodiments thereof taken in conjunction with the accompanying drawings in which:

BRIEF DESCRIPTION OF THE DRAWING

FIG. 1 is a cross-sectional view of an implanted access device of the present invention;

FIG. 2 is a cross-section of a second embodiment of the device of the present invention;

DETAILED DESCRIPTION OF PREFERRED EMBODIMENTS

Figure 3:
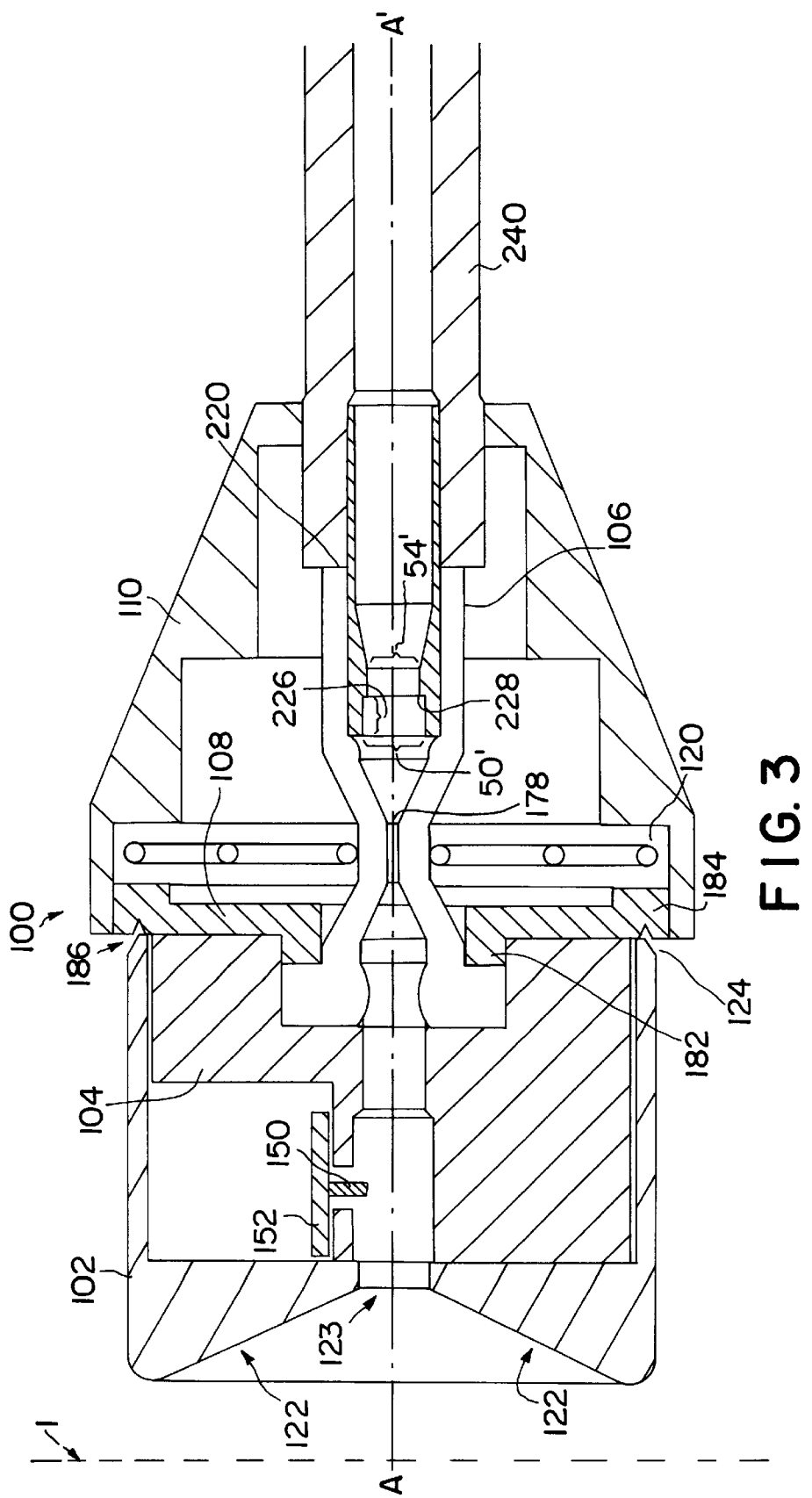
FIG. 3 is a cross-section of a third embodiment of the device of the present invention.

In its simplest form, as shown in FIG. 1, the present invention comprises a modified catheter 2 (which may be situated subcutaneously, as indicated by skin line 1) having an access segment 4, a distal segment 6, and an integral valve segment 8 disposed therebetween. Modified catheter 2 has throughout most of its length a standard inner diameter 10 and a standard outer diameter 12. However, there are several distinct deviations from these values in order to achieve the functional purposes of the invention.

Access segment 4 has disposed at its terminal end a raised identification ring 14 that enables an operator to locate the subcutaneous access device entrance 16. Access segment 4 has an inwardly directed conical access guidance portion 18 and an access alignment portion 20. Access guidance portion 18 has an initial inner diameter 22 greater than standard valve inner diameter 10 and which gradually tapers inwardly until standard valve inner diameter 10 is achieved. Thus, upon insertion, conical access guidance portion 18 guides the percutaneous mating needle 40 into the access alignment portion 20, where the needle 40 is aligned with valve slit 28. Needle 40 has an outer barrel diameter 50, compatible with standard valve inner diameter 10, and an inner barrel diameter 54. Needle 40 is provided with an obdurator 42 having a conical tip for percutaneous insertion of needle 40 into the device without tissue becoming lodged in the lumen of needle 40.

Integral valve segment 8 comprises a tapered valve access portion 24 and a valve portal 26 to further align needle 40 with valve slit 28. It is important to note that integral valve segment 8 is most preferably molded with a solid valve seal portion 30, which has valve slit 28 later formed therethrough. This construction results in a more complete seal and requires less sealing force than does a flattened tube, as is used in the art.

Integral valve segment 8 further comprises an opposing tapered distal portion 32 and has formed into its exterior, in radial alignment with valve seal portion 30, a valve sealing means seat 34, which is a circumferential depression in the segment exterior such that the catheter outer diameter through valve sealing means seat 34 is less than the standard outer diameter 12, but greater than standard inner diameter 10. Valve sealing means seat 34 accommodates valve sealing means 36, which provides a radial biasing force sufficient to close valve seal portion 30, and keep it closed while the device is not in use. In an alternate embodiment, valve sealing means 36 may have one or more mounting tabs 38 formed therefrom or attached thereto. During implantation, the one or more mounting tabs 38 are attached to surrounding tissue such that catheter 2 is immobilized throughout integral valve segment 8, but allowing lateral movement of access segment 4 under the skin.

Outflow segment 6 is implanted such that its terminal end is disposed within the vessel or space to which access is desired. To begin treatment, an operator first locates access segment 4 through the skin using raised identification ring 14 as a guide. The operator punctures the skin with obdurator 42 disposed within needle 40 such that the needle-obdurator assembly enters access guidance portion 18 and is aligned by access alignment portion 20. Continuing to be inserted into the device, the needle-obdurator assembly encounters valve access portion 24 and valve portal 26. As the tip of obdurator 42 enters valve portal 26, the tapered leading edge of obdurator 42 presses against valve access portion 24, overcoming the radial biasing force exerted by valve sealing means 36 and thereby opening valve slit 28 such that needle 40 may pass through the valve seal portion 30. This is accomplished without damage to valve seal portion 30 because needle 40 has already been axially aligned with valve slit 28 by the access alignment portion 20. It is understood that this process is much smoother and causes less discomfort to the patient when the needle is provided with a medically acceptable, water-based lubricant prior to insertion.

It is important to note that because integral valve segment 8 is formed in a closed fashion and valve slit 28 later opened, and also because of the sealing properties of the material from which catheter 2 is made, the valve of the presently claimed invention achieves a complete seal with minimal biasing forces required to be exerted by valve sealing means 36. Accordingly, the force that must be imparted by the needle/obdurator combination in order to overcome this biasing force to allow entry of the needle/obdurator combination into the valve is substantially less than would be required to close known valves, which are essentially flattened tubes and which never achieve a complete seal, unless substantially greater biasing forces are used. This diminution of force results in less jarring of the device during needle insertion and withdrawal, thereby greatly enhancing patient comfort.

In a second embodiment, as shown in FIG. 2, it is contemplated that distal segment 6 is attached to a standard medical catheter 44 by insertion therebetween of adapter 56. Adapter 46 has a first end, disposed within distal segment 6, and a second end, disposed within catheter 44, tapered such that the streamlined flowpath is minimally disturbed. In addition, adapter 56 has formed within its first end a needle seating region 58 having an inner diameter 50' that corresponds with outer barrel diameter 50 of needle 40. Needle seat 58a extends radially inwardly such that its inner diameter 54' corresponds with inner barrel diameter 54 of needle 40. In this embodiment, when the needle-obdurator assembly is inserted into the device and axially through the seal, needle 40 will seat against needle seat 58a such that the streamlined flowpath is minimally disturbed, if at all. (see FIG. 1, not shown in FIG. 2).

In a third embodiment, as shown in FIGS. 3–8, an implanted access device 100 rests below the skin line 1. The access device 100 comprises an assembly of guidance housing 102, locking mount p104, valve 106, valve seating mount 108, valve sealing means 120, adapter 220, catheter 240, and distal housing 110, all arranged about axis AA'.

Guidance housing 102 is a modified hollow cylinder having a partially closed first end formed into an inwardly directed conical needle guidance surface 122 that defines an axial access lumen 123 sized to accommodate a needle suitable for use in hemodialysis, plasma-pheresis, and fluid exchange therapies. Guidance housing 102 has an open second end provided with a chamfered leading edge 124.

Locking mount 104 defines lumen 143 capable of accommodating a needle suitable for use in hemodialysis, plasmapheresis, and fluid exchange therapies formed therethrough. Locking mount 104 comprises a locking portion 140, having lock surface 144 with lock lumen 145 formed therein such that lock lumen 145 communicates with lumen 143, and a valve mounting portion 142, having formed therein valve seat 146 with cross-sectional diameter 146'. Locking portion 140 has attached thereto lock biasing means 152 such that lock biasing means 152 movably covers lock lumen 145. Locking means 150 is disposed within lock lumen 145 and is biased toward lumen 143 by lock biasing means 152. When needle 40 is inserted into lumen 143, the conical tip of obdurator 42 overcomes the biasing force exerted on locking means 150 by lock biasing means 152, thereby causing locking means 150 to retract as needle 40 in inserted. When needle 40 is fully inserted into needle seat 148, semicircular locking groove 44 is aligned with locking means 150. Rotation of needle 40 allows lock biasing means 152 to push locking means 150 into semicircular locking groove 44A, thereby locking the needle 40 into the access device 100. To withdraw needle 40 from access device 100, needle 40 is again rotated so that locking means 150 again retracts and needle 40 is freely removed.

Valve 106 has an access segment 160, a distal segment 164, and an integral valve segment 162 disposed therebetween. Access segment 160 has disposed at its terminal end a raised seating ring 166 having an outer cross-sectional diameter 166' and defining valve entrance 163. Integral valve segment 162 comprises a tapered valve access portion 170 and, optionally, a valve portal 172 to further align needle 40 with valve slit 178. Integral valve segment 162 further comprises an opposing tapered distal portion 174. It is important to note that integral valve segment 162 is most preferably molded with a solid valve sealing portion 176, which has valve slit 178 later formed therethrough. This construction results in a more complete seal and requires less sealing force than does a flattened tube, as is used in the art.

Valve seating mount 108 is a disk-shaped member having an outer cross-sectional diameter 108', a first side oriented toward valve access segment 160, and a second side oriented toward valve distal segment 164. Valve seating mount 108 defines seating mount lumen 183 having a cross-sectional diameter 183' capable of accommodating valve 106. The first side of seating mount 108 has a circumferential groove 186 disposed just axially of its outer peripheral edge. The first side of seating mount 108 also has a raised valve seating spacer 182 formed thereon. Valve seating spacer 182 has an outer cross-sectional diameter 182' substantially similar to valve seating ring cross-sectional diameter 166'. Thus, when valve 106 is inserted into seating mount lumen 183, valve seating spacer 182 and valve access ring 166 have substantially the same cross-sectional diameter and matingly fit recessed valve seat 146 in locking mount 104. This construction further prevents undesirable lateral movement of seating mount 108 relative to locking mount 104, thereby enhancing the stability of access device 100 and minimizing patient discomfort. The second side of seating mount 108 has disposed about its outer peripheral edge a raised valve sealing means spacer 184 of sufficient axial thickness to optimally position valve sealing means 120 relative to valve sealing portion 176.

Valve sealing means 120, may be any conventional or suitable sealing means capable of exerting a radial sealing force sufficient to seal valve slit 178, similar to valve slit 28 of FIG. 1.

Adapter 220, has a first end, disposed within distal segment 164, and a second end, disposed within catheter 240, tapered such that the streamlined flowpath is minimally disturbed. In addition, adapter 220 has formed within its first end a needle seating region 226 having an inner diameter 50' that corresponds with outer barrel diameter 50 of needle 40. Needle seat 228 extends radially inwardly such that its inner diameter 54' corresponds with inner barrel diameter 54 of needle 40. In this embodiment, when the needle-obdurator assembly is inserted into the device and axially through the seal, needle 40 will seat against needle seat 228 such that the streamlined flowpath is minimally disturbed, if at all.

Catheter 240 may be of a type typical of use in hemodialysis, plasmapheresis, and fluid exchange therapies.

Distal housing 110 has a first end with an inner cross-sectional diameter 110' sufficient to accommodate valve seating mount 108 having an outer cross-sectional diameter 108'. In addition, the first end of distal housing 110 has formed therein valve sealing means retainer 112 capable of optimally positioning valve sealing means 120 relative to valve sealing portion 176. Distal housing 110 further has a second end having formed therethrough a lumen 113 capable of accommodating catheter 240.

The cross-section of the needle 40 includes a locking groove 44. Upon insertion of needle 40 into device 100, locking means 150 extends into locking groove 44 to lock the needle 40 in position. The force exerted by lock biasing means 152 on locking means 150 is designed to allow a firm pull to disengage the locking groove 44 from the locking means 150. In another preferred embodiment, locking groove 44 is discontinuous around the circumference of the needle, and disengagement of locking means 150 from locking groove 44 is accomplished by rotating the needle 40 and then withdrawing the needle 40.

For hemodialysis, plasmapheresis, and other fluid exchange therapy operations where flowrates of 200 to 500 milliliters/per minute are possible, the needle 40 can be from 15 to 17 gauge. In such operation the pressure drop through the needle 40 should not exceed 250 mm Hg. Under these conditions a needle 40 can be made of stainless steel and have a wall thickness of approximately 0.1 mm, thereby providing sufficient strength with high safety factors. In contrast, the use of flexible materials would require a needle wall thickness three to five times greater in order to prevent buckling and collapse during insertion.

In the assembled access device 100, valve 106 is disposed within lumen 183 of valve seating mount 108, the combination being seated against locking mount 104, as described above, which combination in turn is entirely disposed within guidance housing 102. Chamfered leading edge 124 of guidance housing 102 matingly fits circumferential groove 186 disposed just axially of the outer peripheral edge of valve seating mount 108. Guidance housing 102 is attached to valve seating mount 108 by known means in order to create a fluid-tight seal. Valve sealing means 120 is optimally positioned by valve sealing means spacer 184 and valve sealing means retainer 112 to seal valve sealing portion 176. Adapter 220 is disposed partly within valve distal segment 144 and partly within catheter 240, as described above. Adapter 220 has needle seating region 226 that matingly fits with needle 40, thereby creating a smooth flowpath from the lumen of needle 40 to catheter 240. Valve 106, valve seating mount 108, valve sealing means 120, adapter 220, and catheter 240 are all disposed within distal housing 110. Catheter 240 emerges from distal housing 110 via axial lumen 113 formed therethrough.

Figure 4:
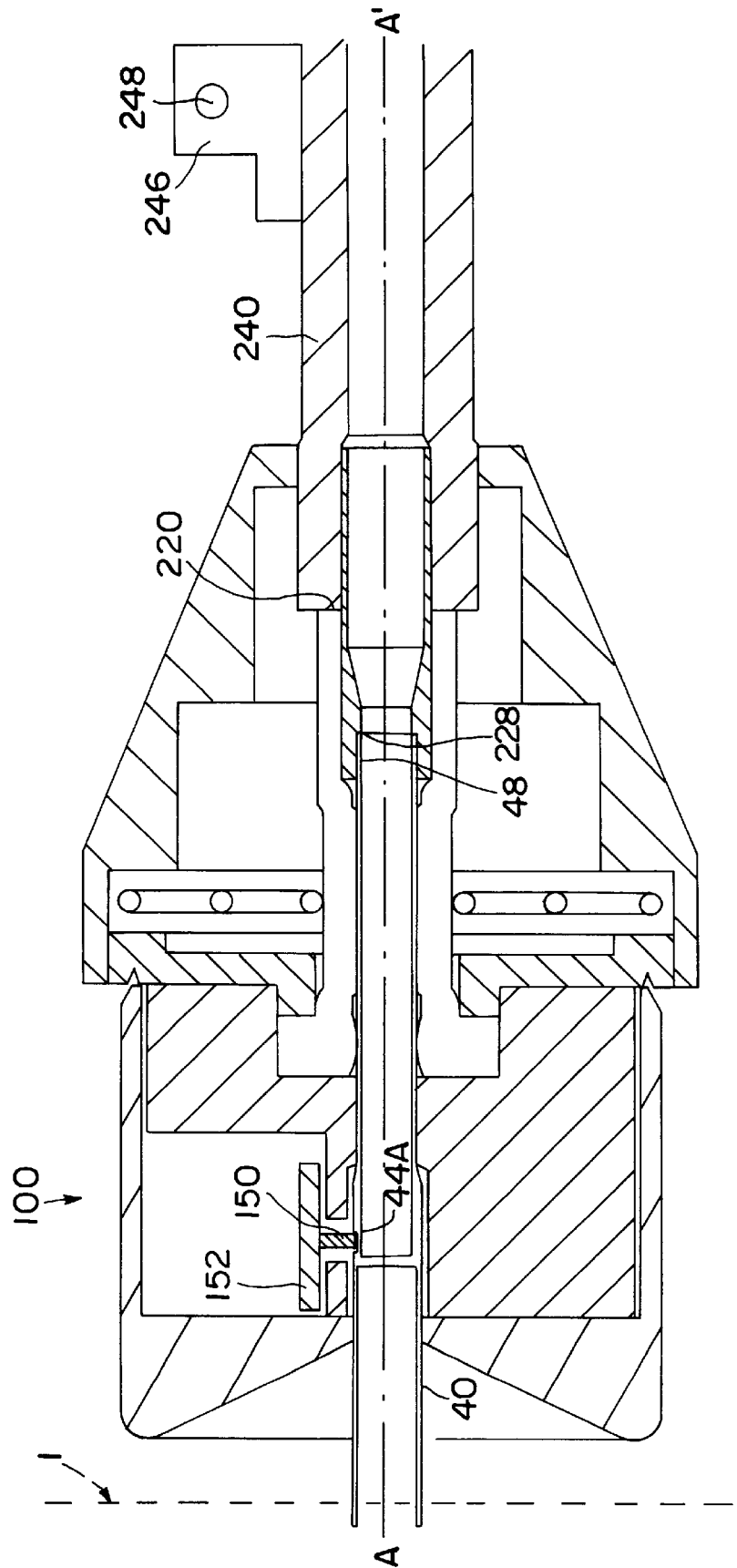
FIG. 4 is a cross-section of the embodiment shown in FIG. 3 with the needle inserted.
Figure 5:
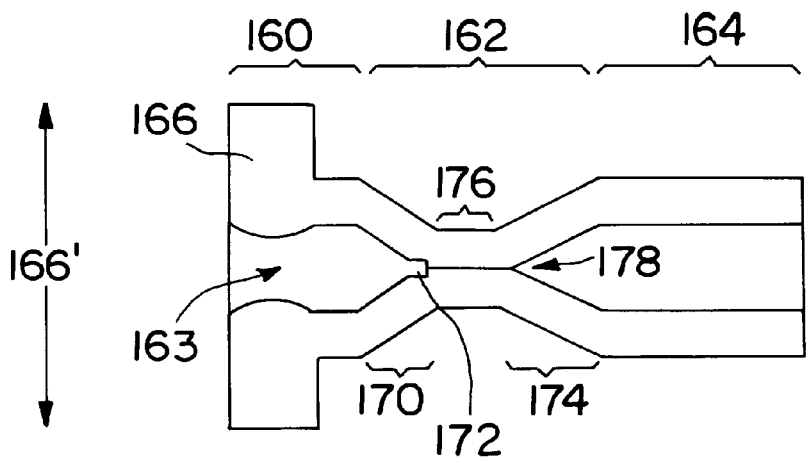
FIG. 5 is a cross-section of the valve of the embodiment shown in FIG. 3.
Figure 6:
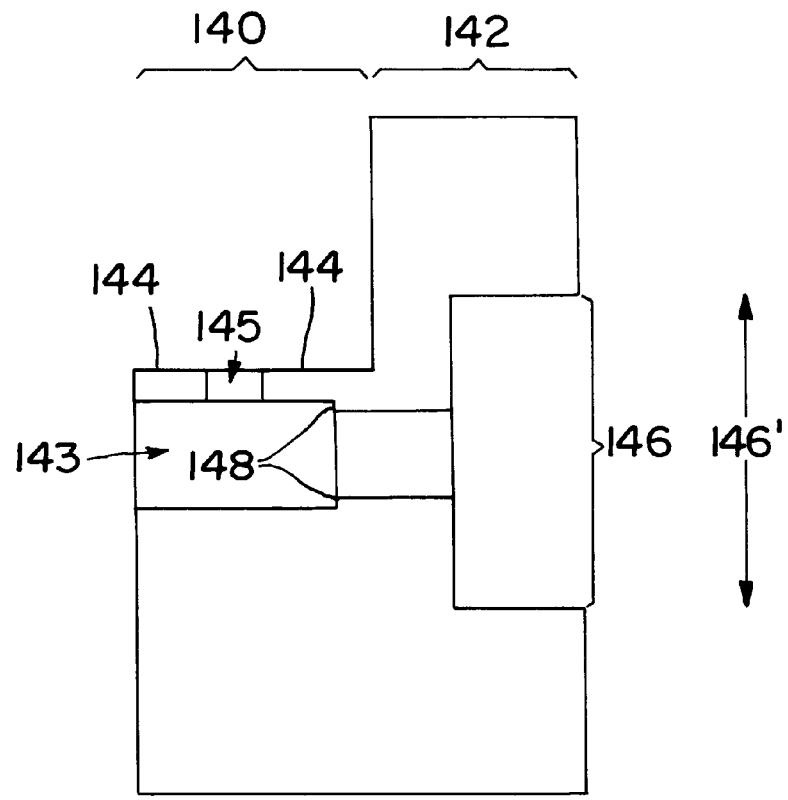
FIG. 6 is a cross-section of the locking mount of the embodiment shown in FIG. 3.
Figure 7:
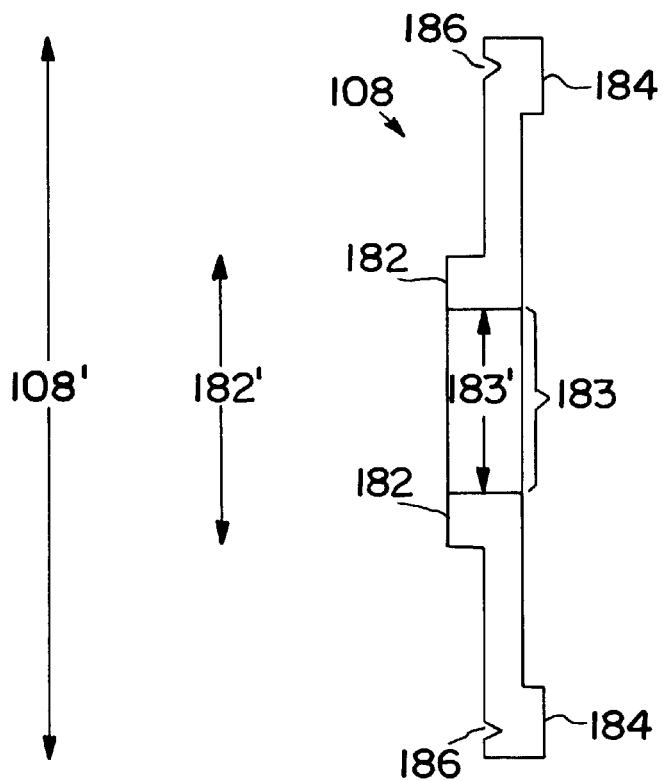
FIG. 7 is a cross-section of the valve seating mount of the embodiment shown in FIG. 3.
Figure 8:
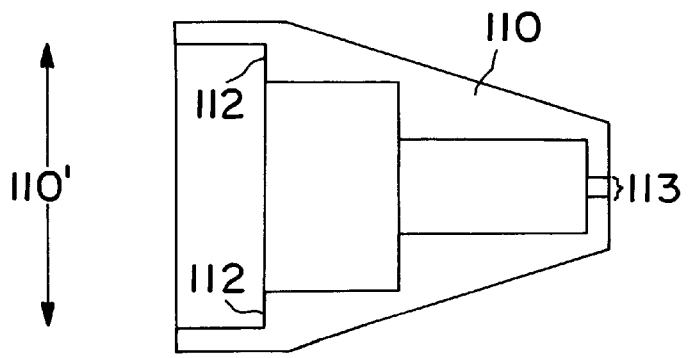
FIG. 8 is a cross-section of the distal housing of the embodiment shown in FIG. 3.

FIG. 4 shows an assembled access device 100, with needle 40 inserted and obdurator 42 removed from needle 40. The needle end 48 is in contact with needle seat 228 of adapter 220, such that the transition from the inner lumen of needle 40 to the inner lumen of adapter 220 is smooth. The assembly is designed and constructed such that all the flow diameter changes are gradual and continuous. The angles of these transitions are less than 25 degrees, with less than 10 degrees preferred. Herein, flow diameter is defined as the diameter of any conduit with fluid flowing measured normal to the flow. The cross-section of the needle 40 includes a ridge and locking groove 44. The locking groove 44 is discontinuous around the circumference of the needle, and disengagement of the locking means 150 from the locking groove 44 is accomplished by rotating the needle 40 and then withdrawing the needle 40 from device 100. In another contemplated embodiment, the locking groove 44 is continuous around the circumference of the needle. The force exerted by lock biasing means 152 on locking means 150 allows the needle 40 to be withdrawn from device 100 with a firm pull to disengage the locking groove 44 from the locking means 150.

In an optional embodiment, catheter 240 has formed therefrom or attached thereto one or more tabs 246 with a through hole 248. This tab 246 is used to fix the catheter 240, by tying or suturing, to the surrounding tissue upon implantation of device 100. The device 100 itself is not fixed to the surrounding tissue. With this arrangement, the device 100 can move underneath the skin enough to align with a needle 40 penetrating the skin without having the needle 40 move transversely to the skin. Adhesions from the tissue to the device 100 are discouraged by treating the housing surface with hyaluronic acid. In addition, to prevent infection, the device may also incorporate or have its exterior surfaces treated with antibacterial material.

Figure 9:
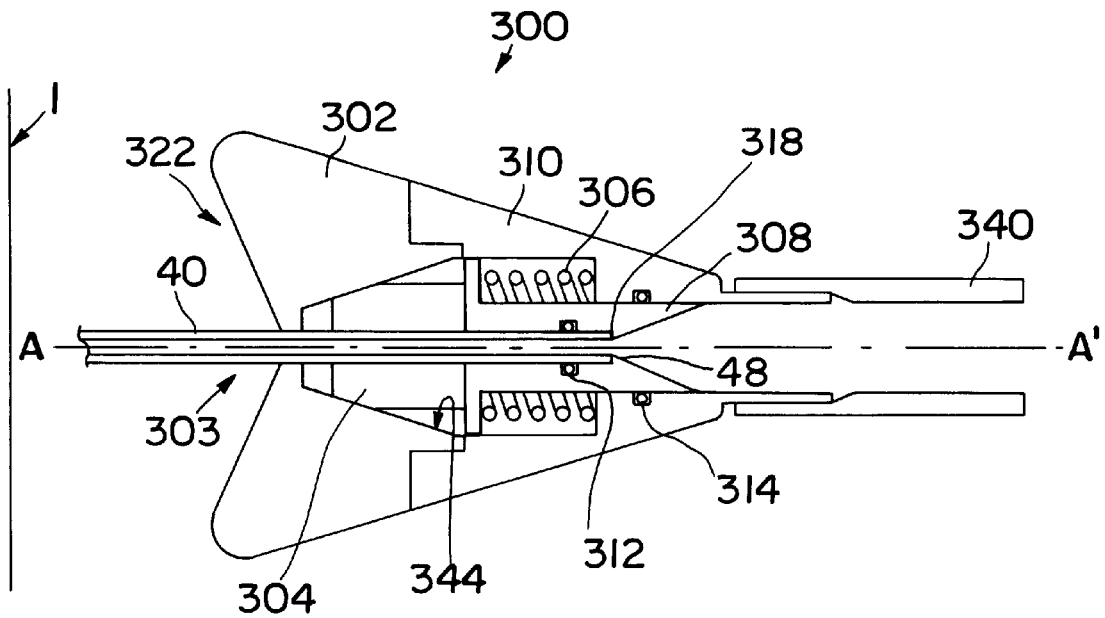
FIG. 9 is a cross-section of a fourth embodiment of the device of the present invention with a sliding seal and integral friction lock.

FIG. 9 shows another contemplated embodiment 300 where there is an integral friction lock to secure the needle 40 within the access device 300. A sealing plug 304 is disposed within housing assembly 302/310 between its access lumen 303 and piston 308. When the device is not in use, spring 306 biases piston 308 against sealing plug 304, urging sealing plug 304 against tapered sealing surface 344, thereby preventing fluid flow through the device.

During use, the needle 40 is guided to the access lumen 303 by the conical needle guidance surface 322 of guidance housing 302, wherein needle 40 contacts sealing plug 304. As needle 40 is pushed further into the device, the axial force exerted by needle 40 on the sealing plug 304 overcomes the septum biasing force exerted on the biasing force transmission flange 309 of piston 308 by spring 306, moving sealing plug 304 away from sealing surface 344 and removing the radial compressive forces normally exerted on the sealing plug 304, sufficiently to allow needle 40 to puncture sealing plug 304. It is important to note that, unlike septa known in the art, where the needle punctures randomly, which eventually results in fragmentation of the septum, sealing plug 304 consistently is punctured in the same place and direction due to guidance of the needle 40 by the conical needle guidance surface 322 of guidance housing 302. This feature effectively eliminates sealing plug fragmentation.

Once needle 40 punctures sealing plug 304, needle 40 contacts needle seat 318 of piston 308, where the needle tip 48 contacts needle seat 318 to form a smooth transition between the needle 40 and the piston 308. Once needle 40 is inserted, sealing plug 304 provides enough residual pressure onto the needle 40 to effectively lock the needle 40 into the device 300. An axial pull on the needle 40 tends to pull the sealing plug 304 against the sealing surface 344, increasing the radial forces exerted on the needle 40, thereby holding the needle even more securely. A simple twist of needle 40, however, introduces dynamic friction and allows the needle 40 to be removed from the device. O-rings 312 and 314 seal the needle 40 from the piston 308 and the piston 308 from the sealing housing 310, respectively. When the device is not in use, spring 306 biases the piston 308 towards the skin line 1, compressing the sealing plug 304 such that the sealing plug 304 seals itself, closing the passageway formed by insertion of needle 40. Note that, as the piston 308 slides relative to the catheter 340 and the sealing housing 310, the transition from the piston 308 and the catheter 340 inner wall and/or the sealing housing 310 inner wall remains smooth.

Figure 10:
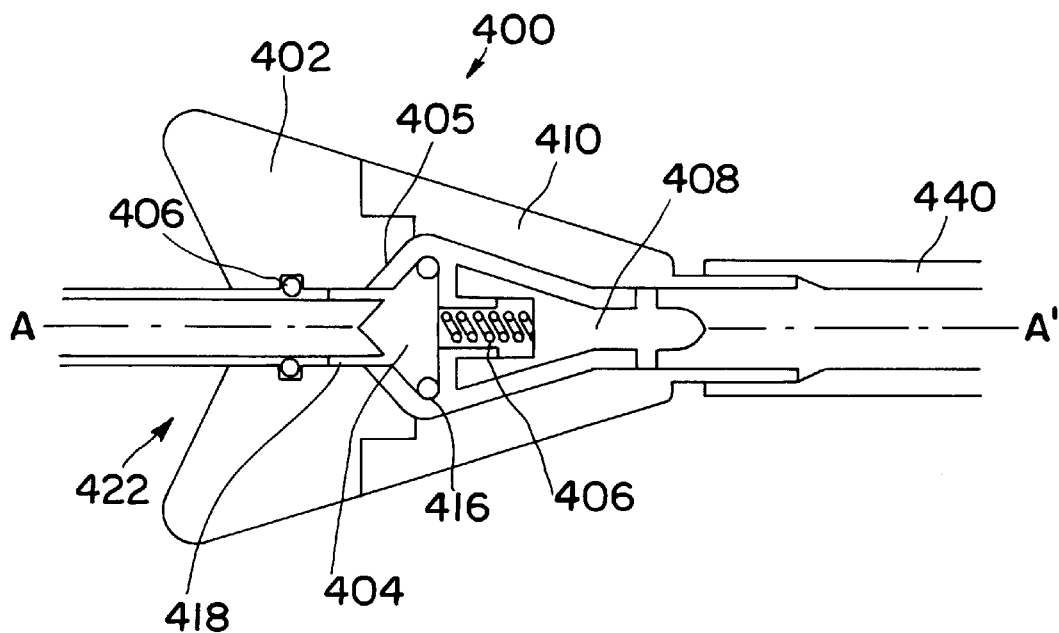
FIG. 10 is a cross-section of a fifth embodiment of the device of the present invention with a longitudinally sliding seal.

FIG. 10 is yet another contemplated valving for the present invention. In this embodiment, the needle 40 contacts a sliding spring-loaded poppet 404. As the needle 40 is pushed into the device 400 using conical needle guidance surface 422 the valve structure 408 is biased away from guidance housing 402 (as shown). The O-ring 416 leaves the housing wall 405 allowing fluid to pass through the valve. Spring 406, forces the poppet 404 and 0-ring 416 back into contact with the housing wall 405 when the needle 40 is extracted from the device. The poppet 404 does not extend throughout the valve circumference, as it would then interfere with the fluid flow. Instead, the poppet 404 has a plurality of rod-like extensions 418 that provide open areas for fluid to pass through the valve when the needle is inserted. The O-ring 406 provides a seal to prevent leakage around the needle 40. As piston 408 (valve structure) slide relative to the catheter 440 and the sealing housing 410 the transition from piston 408 and catheter 440 inner wall and/or sealing housing 410 inner wall remains smooth.

Figure 11:
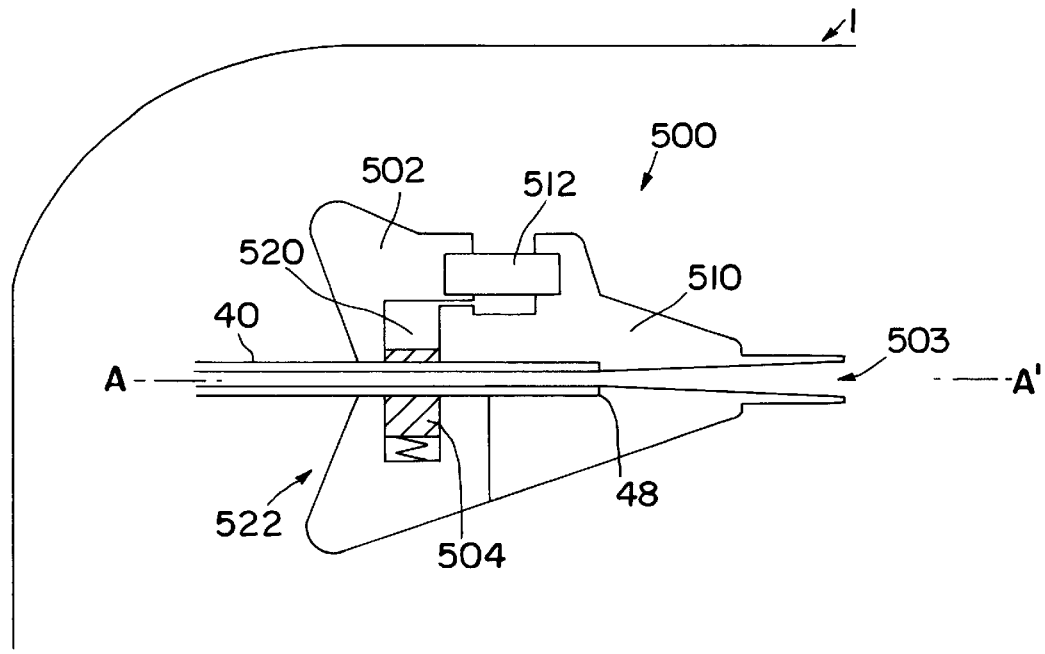
FIG. 11 is a cross-section of a sixth embodiment of the device of the present invention with a trumpet valve.
Figure 12:
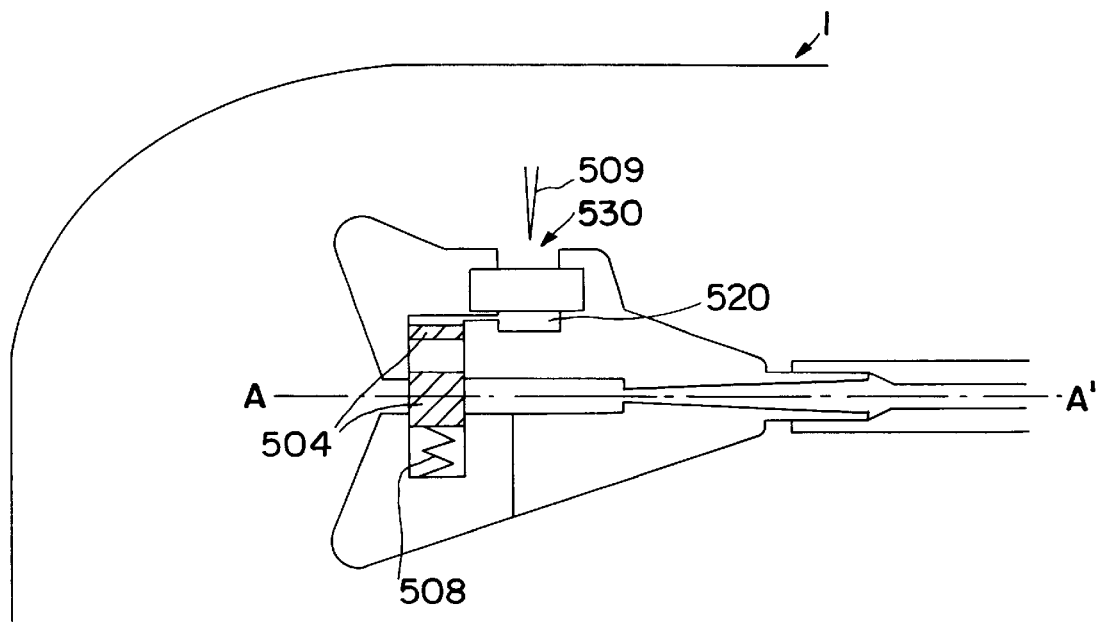
FIG. 12 is a cross-section of the embodiment shown in FIG. 11 with the needle inserted.

FIGS. 11 and 12 show another contemplated embodiment 500, wherein the valve sealing means is a trumpet valve 504. Prior to each treatment session, a fine needle 509 may be percutaneously introduced into lumen 530 and penetrate the septum 512 to open valve 504 by injecting fluid into reservoir 520 sufficient to overcome the biasing force exerted by spring 508. Needle 40 may then be introduced into the device 500, in similar manner as described above with respect to 300 (FIG.9) and 400 (FIG. 10), and guidance housing 502 having conical needle guidance surface 522 guide needle 40. When the treatment session is completed, needle 40 is removed from the device and trumpet valve 504 is closed by withdrawing fluid from reservoir 520 via fine needle 509, which is then removed from the device. As shown there is a sealing housing 510 which cooperates with guidance housing 502, and there is a seal 504 which seals passageway 503.

Figure 13:
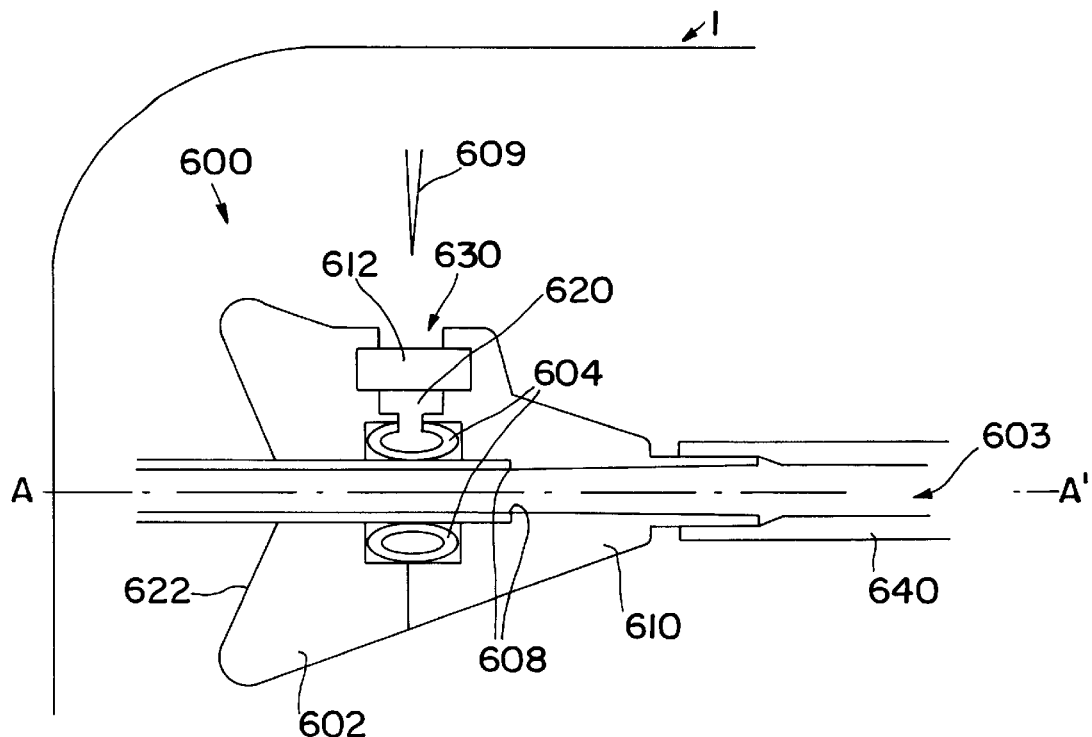
FIG. 13 is a cross-section of a fifth embodiment of the device of the present invention with an inflatable seal.

FIG. 13 is another contemplated embodiment 600 where an inflatable seal 604 seals passageway 603. The needle 40 guided by conical needle guidance surface 622 of guidance housing 602, such that the needle 40 pushes the expandable seal 604 apart when inserted. The needle 40 then hits the stop 608 built into the sealing housing 610. When the needle 40 is extracted, the seal 604 expands, closing the passageway 603. As may be needed from time to time, a fine needle 609 may be percutaneously introduced into lumen 630 and penetrate the septum 612 to re-expand the seal 604 by injecting fluid into reservoir 620, which is in fluid connection with the lumen of seal 604. As in the other embodiments, the flowpath transition from the sealing housing 610 to the catheter 640 is smooth.

Figure 14:
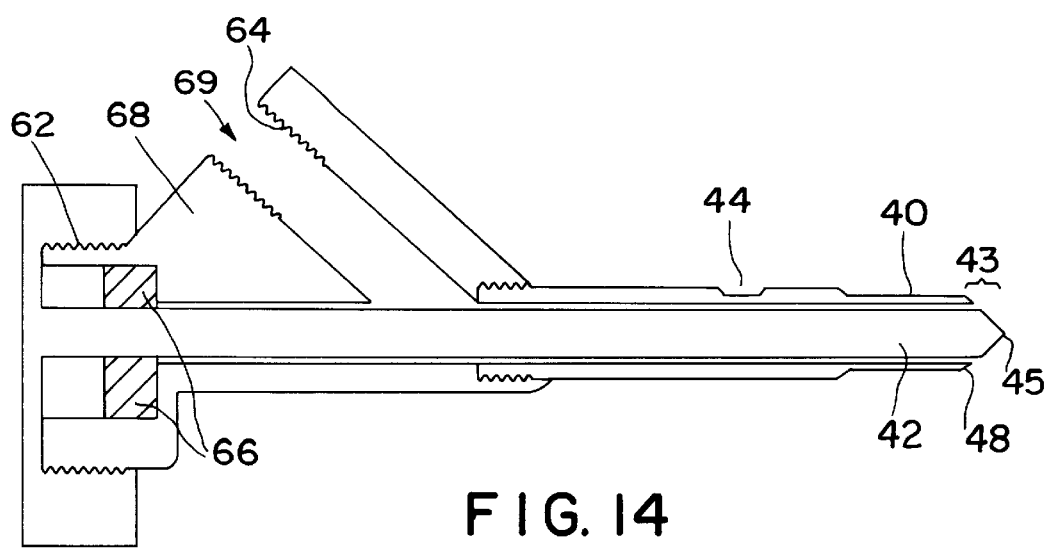
FIG. 14 is a cross-section of a preferred needle and obdurator assembly.

FIG. 14 shows a preferred corresponding needle assembly constructed and arranged to mate with the previously described implanted access housings. The needle barrel 40 is of a thin metal material. Thinner material maximizes the actual flow diameter which is a general goal of any hemodialysis needle. The discomfort to the patient is reduced by smaller diameter needles, but such needles restrict flow or provide large pressure drops when high flows are forced through small needles. Low flowrates would require inordinate treatment time for hemodialysis, and high flowrates through narrow needles damages blood. There is a tradeoff and thin needle walls contributes to maximized flow diameters for a given outer needle diameter. An obdurator 42 is fitted within the needle barrel 40, providing a smooth transition 43 between the outer surface of needle 40 at the needle tip 48 and the obdurator 42. The needle barrel 40 has a semi-circular locking groove 44A. The obdurator 42 is secured to a housing 68 via threads 62. The obdurator 42 is necessary since the needle 40 is hollow and cannot be used to penetrate the skin because its large diameter lumen will become plugged. The obdurator 42 exactly fills the hollow face presented to the skin and has a point 45 suitable for penetrating the skin. The housing 68 provides a channel 69 with the threaded fitting 64 for connecting to the hemodialysis equipment. When the obdurator 42 is removed, there is a slit disk valve 66 that closes off the opening used by the obdurator 42, allowing the hemodialysis to proceed.

It will now be apparent to those skilled in the art that other embodiments, improvements, details and uses can be made consistent with the letter and spirit of the foregoing disclosure and within the scope of this patent, which is limited only by the following claims, construed in accordance with the patent law, including the doctrine of equivalents.

What is claimed is:

1. A hemodialysis access system for access to a human or animal patient's vascular system for high fluid flow rate exchange of blood between the vascular system and an external processing apparatus at a volumetric flow rate in excess of 250 ml/minute, and comprising, in combination, (a) a needle assembly comprising a lumen defined by an interior surface and constructed and arranged for puncturing the skin of the patient and for carrying blood therethrouqh at a flow rate consistent with high blood flow requirement of the blood exchange process;

(b) a subcutaneously implantable access device permitting fluid connection to a vessel or space within a patient's body, the device comprising:

(i) a substantially straight-through channel structure having an interior surface and a distal end and a proximal end with reference to the patient's skin puncture site and constructed and arranged for insertion of the needle through the proximal end of the channel and withdrawal of the needle therefrom, (ii) a seal arranged within the channel and movable between first and second positions, where said seal, in said first position, with said needle not inserted through said seal, prevents fluids from passing said seal and, in said second position, with said needle inserted through said seal, allows fluids to pass through said needle and emerge substantially at said channel distal end, and where blood flowpath transitions between said needle interior surface and said channel interior surface are substantially continuous and smooth when said means for sealing is in said second position; and the device further comprising structure for joining said channel distal end to a catheter that extends to an internal vessel of the body, and wherein such joining is continuous and smooth along said interior surfaces of the channel and catheter.

2. An access system as defined in claim 1 further comprising:

(c) a catheter constructed and arranged for implantation between said device at a proximal catheter end and to or into a patient blood vessel at a distal catheter end, and (d) means for attaching the catheter to the surrounding patient tissue, said attachment allowing movement of the catheter's proximal end and of said device.

3. Apparatus as defined in claim 1 wherein said needle has a lumen and disposed along a first axis, said needle matingly corresponding to the inner surface and having a wall thickness of approximately 0.1 mm, an obturator that is disposed within the needle along the first axis and matingly inserted into the lumen of said needle, said needle and obturator designed to provide an assembly with a pointed end constructed for opening said means for sealing, and means defining an access channel external to the patient communicating with the lumen of said needle, when it is inserted into the patient and through said means for sealing and wherein said access channel is disposed at an acute angle from said needle first axis.

4. Apparatus as defined in claim 1 further comprising a groove constructed in the outer surface of said needle, and a needle lock located within the channel length and extending into the channel, said needle locking means positioned before the means for sealing, said needle lock engaging said needle groove to secure the needle to the access housing, and wherein said channel and needle lock are constructed to release by twisting and/or pulling on the needle out of the channel.

5. A system as defined in claim 1 for high flow rate blood exchange between a human or animal patient with simultaneous flow in and out of the patient through separate paths, comprising a subcutaneously implantable access device capable of being implanted in the patient just under the skin and having two passages therein, each with an entrance proximal to the skin and an exit distal therefrom, for accommodating two hollow needles, with interior lumens, percutaneously inserted therein, the transitions between the interior lumens of the needles and passage interiors of the device forming substantially straight and streamlined flowpaths, thereby permitting fluid connection to one or two blood vessels within a patient's body.

6. A system as defined in claim 5 further comprising means to secure said needles to each other and locking means to secure the needles within the device.

7. A hemodialysis access system for repeated access to a patient's distal vascular system in the course of long term fluid exchange therapy between the vascular system and a proximal blood processing site, via a catheter that is subcutaneously implanted in the patient and has a distal end coupled to a patient blood vessel and a proximal end, the system comprising, in combination, (a) a needle assembly comprising an elongated thin walled rigid cannula with proximal and distal ends (proximal toward the blood processing site and distal toward the vascular system) and an obturator constructed and arranged for insertion into the cannula and passing through its full length, and with a pointed distal end of the obturator emerging from a cannula distal end and removable from the cannula, the cannula being constructed and arranged, when the obturator is removed, for blood flow through the cannula interior at a high flow rate of at least 250 milliliters per minute, the cannula being constructed at its distal end for longitudinal flow of blood at such end to enter or exit the cannula and means for communicating from said back end portion of the cannula interior to an external blood processing site, (b) a subcutaneously implantable access device having an entrance and exit regions and a passage therebetween which permits the cannula to enter the entrance end region and occupy a substantial passage length with a full annular meeting between the cannula distal end and a corresponding seat within the passage to establish a smooth transition between said cannula distal end and the device's exit region, the device being arrangeable subcutaneously with its exit region attached to said proximal catheter end and its entrance region accessible to the needle assembly through the patient's skin, the cannula interior and exit region thereby defining together a continuous streamlined flowpath essentially free of stagnation points or abrupt transitions and constructed and arranged for blood passage through the flow path defined thereby at a flow rate of at least 250 milliliters per minute, (c) the needle assembly being constructed and arranged to penetrate the patient's skin and subcutaneous tissue to reach the entrance region of the said device and transit the passage of the latter to a point adjacent the exit region of the device and for withdrawal of the obturator to a point external of the patient's skin whereby the external blood processing site can be placed in fluid communication with the cannula and catheter to establish a blood exchange path, and flushing path, from outside the patient to the patient's vascular system, and further comprising, (d) a seal located within the device's passage at a site normally passed by cannula/obturator insertion therein, and comprising means to close off the passage, when acted on by a biasing force, to produce a seal seating stress when the cannula/obturator is not in the passage and openable when contacted by the cannula/obturator outer surfaces, means for applying such biasing force, the seal and cannula/obturator constructed and arranged so that the external cannula/obturator surfaces bear against the means to force it aside to an open position, overcoming the bias force, to permit the cannula/obturator to transit the device's passage, but without the obturator's distal point contacting the resilient sealing material, the cannula being sufficiently rigid to hold the seal open when the obturator is withdrawn from the inserted needle.

8. The device as claimed in claim 7 further comprising a needle-locking means to secure a percutaneously inserted needle within the device.

9. The system of claim 7 wherein the passage comprises a region adjacent its exit for docking with the distal end of the inserted cannula and forming a smooth walled flow path transition therewith.

10. A hemodialysis access system for use in a blood exchange therapy system, involving an extracorporeal blood processing apparatus operating at a flowrate of at least 250 milliliters per minute and being capable of allowing hundreds of such therapy cycles, the blood exchange therapy system comprising a catheter implanted in the patient and connected to a blood vessel of the patient at a distal end and having a proximal portion within the patient adjacent the patient's skin, and the access system comprising:
(a) means forming a continuous, streamlined flowpath running from outside the patient to the catheter, essentially free of surface discontinuities and flow stagnation sites and substantial pressure drops, said means having two elements joining at an abutment with smooth transition at such abutment and all changes in flowpath cross-section being of a gradual nature, said means comprising:
  (i) a device implantable within the patient and having a passage therein with an internal abutment;
  (ii) a needle that is insertable percutaneously into the patient and into the device passage to meet said abutment in full annular contact and therewith establish a smooth transition portion of the streamlined flowpath and is withdrawable from the device and the patient; and
  (iii) a flexible seal in the device that automatically blocks the flowpath when the needle is not inserted and is entirely out of the flowpath when the needle is inserted and is not degraded by the repetitive therapy cycles of needle insertion, high volume blood exchange and needle withdrawal,
whereby a blood exchange therapy is maintainable with high resistance to blood clotting, infection, erythrocyte damage and platelet activation and with low pressure drop along the flowpath, consistent with the flow requirements of blood exchange therapy.

11. A subcutaneously implantable access device as recited in claim 10 having a distal catheter wherein the device is freely movable and the distal catheter is secured to surrounding tissue.

12. A hemodialysis access system comprising:
(a) an assembly comprising a patient implantable access device and a rigid cannula providing a continuous flowpath, crossing the patient's skin, between an external-to-patient dialysis site and an internal blood vessel of the patient, the device having an internal passage structure including a part constructed and arranged to meet circumferentially fully an end of an inserted cannula and form therewith a portion of the flowpath that is, alone with essentially all other portions of the said flowpath, smooth and free of abrupt changes in flow area and direction and define a flowpath sized for hemodialysis flow rates, and free of obstructions to provide low flow resistance and avoid stagnation points;
(b) means within the access device for blocking the flowpath at a point under the patient's skin; and
(c) means for removing the flowpath portion crossing the patient's skin; to allow closure and healing of the skin crossing site.

13. The system of claim 12 further comprising a flexible seal and wherein flowpath blockage is provided by said flexible seal, the flexible seal being entirely removable from the flowpath to establish a fully open configuration thereof free of obstructions and abrupt flow diameter or flow direction changes.

14. The system of either of claims 12 or 13 and further comprising means for locking and unlocking the flowpath forming portion of the system.

15. The system of either of claims 12 or 13 and further comprising means for increasing the available skin-crossing sites used in establishing the flowpath.

16. The system of claim 15 comprising a hollow needle which is insertable percutaneously by longitudinal pushing of it to a site where it defines a portion of said flowpath, and withdrawable by longitudinal pulling of said needle, and an implanted catheter comprising another portion of the flowpath and means for establishing a smooth continuous transition between said portions.

17. The system of claim 16 and further comprising means for locking the inserted needle in place and wherein said locking means are constructed and arranged to lock the needle upon longitudinal insertion movement and unlock and lock it upon longitudinal withdrawal movement accompanied by a lateral twisting movement.

18. The system of claim 17 and further comprising an obturator within the hollow needle and wherein said obturator has a pointed end arrangeable to protrude from a hollow needle end.

19. A hemodialysis access system for repeated access to a patient's vascular system, for hemodialysis repetitive blood exchange therapy, via a catheter that is subcutaneously implanted in the patient and has a distal end attached to a patient blood vessel and a proximal end near the patient's skin, the system comprising, in combination,
(a) a subcutaneously implantable access device having an entrance region, exit region and a passage therebetween providing for introduction of a needle thereby defining together with each other and the catheter a continuous streamlined flow path essentially free of stagnation points and constructed and arranged for blood flow through the flow path at a flow rate of at least 250 milliliters per minute,
(b) a needle for defining a continuous flowpath extension relative to the catheter, and comprising an assembly of a cannula and an obturator, and with a front part of the obturator emerging from a cannula front end and removable from the cannula, the cannula being constructed and arranged as a portion of said passage, when the obturator is removed, and means for communicating from the cannula interior to an external patient site,
(c) the needle being constructed and arranged to puncture the patient's skin, to penetrate subcutaneous tissue and reach the entrance region of the implanted device and transit the passage of the latter to a point adjacent the exit region of the device and for withdrawal of the obturator of the needle means to thereby establish fluid communication between an external to the patient site and the catheter to provide a blood exchange path and flushing path from outside the patient to the patient's vascular system, the needle having a distal end,
(c') the access device and needle cannula constructed and arranged with respect to each other so that there is a full annular meeting between the cannula distal end and a corresponding seat within the passage to establish a smooth transition between the cannula distal end and the device's exit region,
and further comprising,
(d) means located within the device's passage at a site normally passed by needle insertion therein, for sealing said passage when the cannula/obturator is not in the passage and openable when contacted by the outer surface of the needle means, the seal and needle constructed and arranged so that the needle surface bears against the sealing material which is forced aside to an open position to permit the needle to transit the device's passage, but without the point thereof contacting the sealing surfaces, the cannula being sufficiently rigid to hold the seal open when the obturator is withdrawn from the inserted cannula.

20. The system of claim 19 wherein the passage comprises a region adjacent its exit for stopping the front end of the cannula of the inserted needle and forming a smooth walled flow path transition therewith.

21. The system of any of claims 9, 19 or 20 constructed and arranged with all flow path wall elements having an angle relative to flow axis of zero to 25 degrees.

22. The system of claim 21 wherein all such angles are zero to ten degrees.

23. The system of any claims 9, 19 or 20 where the means for sealing comprises an integral molded flexible material with a later formed central valve slit.

24. The system of claim 23 and further comprising lubrication of the needle and seal contact.

25. The system of of claims 9, 19, or 20 further comprising a lock in the device located between its entrance region and seal for holding the inserted needle, the lock being constructed and arranged for activation by needle means insertion through said passage and releasable by needle rotation in and withdrawal from, said passage.

* * * * *